US008361810B2

(12) United States Patent
Farwell et al.

(10) Patent No.: US 8,361,810 B2
(45) Date of Patent: Jan. 29, 2013

(54) BIOWEAPON-DETECTING FIBROUS-NETWORK PRODUCTS AND METHODS FOR MAKING SAME

(76) Inventors: Dennis Farwell, Beaverton, OR (US); Keith Baumann, Beaverton, OR (US)

( * ) Notice: Subject to any disclaimer, the term of this patent is extended or adjusted under 35 U.S.C. 154(b) by 373 days.

(21) Appl. No.: 12/417,297

(22) Filed: Apr. 2, 2009

(65) Prior Publication Data

US 2012/0285642 A1    Nov. 15, 2012

Related U.S. Application Data

(63) Continuation of application No. 10/431,047, filed on May 6, 2003, now Pat. No. 7,527,981.

(60) Provisional application No. 60/379,537, filed on May 9, 2002.

(51) Int. Cl.
    *G01N 33/554* (2006.01)
(52) U.S. Cl. ........ 436/535; 436/518; 436/528; 436/529; 436/164; 436/167; 435/7.1; 435/283.1; 435/287.1; 435/287.2; 435/287.9; 435/288.7; 42/83; 42/81

(58) Field of Classification Search .................. 436/535, 436/518, 528, 529, 164, 167; 435/7.1, 283.1, 435/287.1, 287.2, 287.9, 288.7; 422/83, 422/91
See application file for complete search history.

(56) References Cited

U.S. PATENT DOCUMENTS

| | | | | |
|---|---|---|---|---|
| 4,046,514 | A * | 9/1977 | Johnston et al. | 422/420 |
| 4,472,498 | A * | 9/1984 | Masuda et al. | 435/7.7 |
| 5,013,403 | A * | 5/1991 | Chase | 162/49 |
| 5,141,850 | A * | 8/1992 | Cole et al. | 436/525 |
| 6,306,598 | B1 * | 10/2001 | Charych et al. | 435/6.11 |
| 6,770,485 | B2 * | 8/2004 | Knezevic et al. | 436/86 |

* cited by examiner

*Primary Examiner* — Melanie J Yu
(74) *Attorney, Agent, or Firm* — Rader, Fishman & Grauer PLLC

(57) ABSTRACT

Methods are disclosed for producing a bioweapon-sensitive fibrous-network product, wherein the subject products exhibit a color change in response to exposure to a biological agent (or portion thereof) as used in a biological weapon. Also disclosed are fibrous-network products that contain units of biopolymeric material that impart a color change to the products in response to exposure to a biological agent (or portion thereof) as used in a biological weapon.

29 Claims, 1 Drawing Sheet

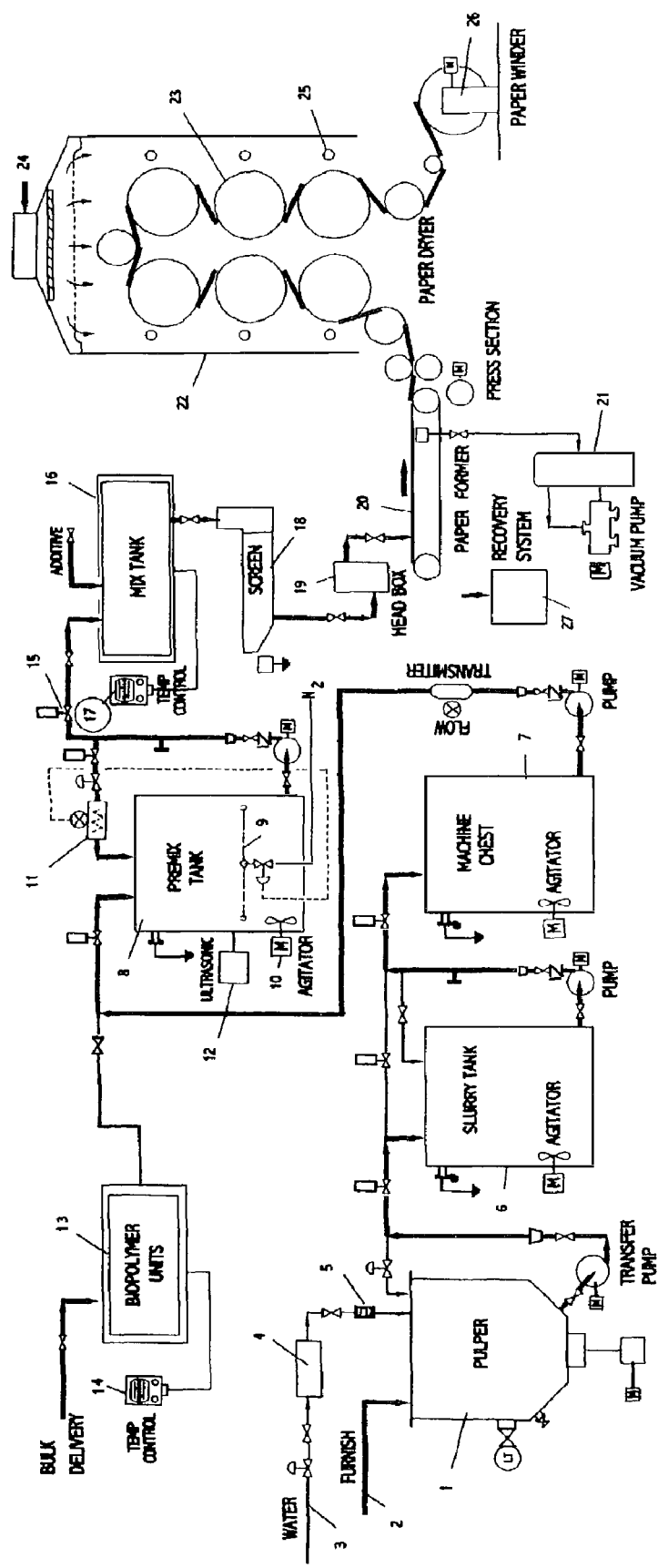

BIOWEAPON-DETECTING FIBROUS-NETWORK PRODUCTS AND METHODS FOR MAKING SAME

CROSS REFERENCE TO RELATED APPLICATIONS

This application is a continuation of U.S. patent application Ser. No. 10/431,047, filed May 6, 2003 now U.S. Pat. No. 7,527,981, which claims the benefit of U.S. Provisional Application No. 60/379,537, filed May 9, 2002, both of which are hereby incorporated by reference in their entirety.

PRIORITY CLAIM

This application claims the benefit of U.S. Provisional Application No. 60/379,537, filed May 9, 2002.

FIELD

The present disclosure relates, inter alia, to fibrous-network products such as paper products, woven-fabric products, and products that are composites of woven and non-woven (paper) products. More specifically, the disclosure pertains to such products that exhibit a color change in response to contact with a biological-weapon agent (or a portion of a biological-weapon agent), and to methods for producing such fibrous-network products.

BACKGROUND

Biological weapons ("bioweapons") include bacteria, viruses, and toxins that are dispersed deliberately in an environment to cause disease or death to humans, animals, or plants in the environment. Examples of bioweapons include *Bacillus anthracis*, which causes anthrax, *Yersinia pestis*, which causes plague, and *Variola major*, which causes smallpox. Bioweapons also include "biotoxins," which are toxins produced by certain biological organisms. Exemplary biotoxins are botulinum toxin, produced by the bacterium *Clostridium botulinum*, and ricin isolated from castor oil seeds. Western counter-proliferation agencies currently recognize 23 types of bacteria, 43 types of viruses, and 14 types of biotoxins as potential bioweapons.

To an aggressor, bioweapons are appealing because: (a) they are directed indiscriminately to populations, (b) they leave infrastructure intact, (c) they usually are effective in very small amounts, (d) they can be produced at low cost in a short period of time, and (e) their detection is difficult. Because of these properties of bioweapons, there is growing concern that bioweapons will become the preferred weapon of mass destruction.

Recent activities by terrorists have targeted the U.S. Postal System by using common envelopes as vehicles for delivering anthrax spores. Whereas, before the current outbreak of bioterrorism-related anthrax, only 18 cases of inhalational anthrax had been reported in the United States in the 20th century, ten cases of biotcrrorism-related inhalational anthrax have now occurred. Because the U.S. Postal Service currently handles an estimated 239 billion items of mail per year, the risk is high that another disease outbreak will result from envelopes deliberately contaminated with anthrax or other bioweapon. The risk is even larger for mail and parcel services worldwide.

The U.S. Postal Service has issued a set of guidelines for evaluating suspicious mail and parcels. These include use of excessive postage, lopsidedness or oddly shaped, marked with restrictive endorsements (such as "Personal" or "Confidential"), having protruding wires, strange odors, or stains, or denoting a city or state in the postmark that does not match the return address. However, current technology can respond to bioterrorism only if such a threat is suspected or known to be imminent. Presently, there is no known practical way in which to screen all mail for bioweapons in a systematic manner.

SUMMARY

Disclosed herein are, inter alia, methods for producing bioweapon-sensing fibrous-network products that address the needs summarized above. Such a bioweapon-sensing fibrous-network product provides, for example, an early and unambiguous alert to mail-handling personnel and mail recipients that a bioweapon (or portion thereof) has at least contacted the product, and possibly other items and equipment in the postal media. As used herein, a "fibrous-network product" is any product formed as a network of constituent fibers, which encompasses non-woven fabrics (generally termed "paper products" herein), woven fabrics (generally termed "woven products" herein), composites of multiple non-woven fabrics, composites of multiple woven fabrics, and composites of woven and non-woven fabrics.

In contrast to bioweapon detectors that are printed on the surface of paper products (e.g., as discussed in U.S. Pat. No. 6,306,598), the bioweapon-sensing fibrous-network products disclosed herein contain units of a bioweapon-sensing agent dispersed throughout at least a portion of the thickness dimension of the product. Thus, not only is much of the bioweapon-sensing agent shielded by fibers of the product from the direct physical insults inherent in, for example, mail-sorting and delivery processes, but also the agent can detect exposure to a bioweapon (or portion thereof) on both the inside and outside surfaces of the fibrous-network product.

As defined herein, a "paper product" is not limited to such products made exclusively from cellulose fibers. "Paper product" encompasses any of various products prepared by laying down a mat of fibers from a fluid (liquid or gas) suspension of fibers. The fibers can be cellulosic (e.g., obtained from wood pulp or other cellulosic fiber such as cotton fibers, rayon fibers, etc.), non-cellulosic (e.g., glass or polymeric), proteinaceous (e.g., silk, fur, or felt), or a mixture of one or more of these various types of fibers. Similarly, a woven product is not limited to such products made from cellulose fibers. The fibers can be cellulosic, as noted above, non-cellulosic, proteinaceous, or a mixture of one or more of these various types of fibers.

To incorporate the bioweapon-sensing agent through the thickness dimension of a paper product, units of the bioweapon-sensing agent are dispersed in a fluid suspension of the fibers used to form the paper product, and are formed together with the fibers in the paper product. The incorporation can extend through the length and width dimensions of the paper product, or be limited to certain zone(s) (e.g., stripe(s)) on the paper product. In addition, a second fluid suspension (containing fibers and units of a second bioweapon-sensing agent) can be applied to a paper product already formed from a first fluid suspension (containing fibers, which can be the same or different from the fibers in the second fluid suspension, and optionally units of the second or a first bioweapon-sensing agent). In the resulting composite, each bioweapon-sensing agent is incorporated throughout at least a portion of the thickness of the composite product.

For making paper products, the bioweapon-sensing agent desirably is a form that can be readily dispersed in fluid suspension with fibers used to form the paper product. Any of various "units" of the bioweapon-sensing agent can be used that meet this criterion. For example, and not intending to be limiting, the units can be particles of any of various configurations such as microspheres, membrane fragments, fibers, microtubular, or generally irregular. A particularly desirable configuration of the bioweapon-sensing agent is biopolymeric liposomes. Due to their spherical shape and extremely small dimensions, biopolymeric liposomes are readily dispersible in fluid suspension with a population of fibers suitable for making a paper product, and are extremely durable while retaining sensitivity to contact with one or more specific bioweapon agents. A suspension of these liposomes is combined with a "slurry" or other fluid suspension of fibers and mixed to form a composite mixture. The composite mixture is formed into a paper product comprising the liposomes and fibers, wherein the liposomes are intermingled with the fibers throughout the thickness dimension of the paper product. The biopolymeric liposomes can be immobilized in solid-support particles that are dispersible in a fluid suspension of the fibers and subsequently formed into a paper product. The solid-support particles can be, for example, sol-gel particles. In a more specific embodiment, the biopolymeric liposomes comprise an entity ("ligands") that is sensitive to contact with one or more specific types of bioweapon bacteria or spores. For example, the liposomes (and thus regions of the paper product containing the liposomes) exhibit a color change upon contact with anthrax bacteria and/or spores.

Also disclosed herein are paper products that contain biopolymeric liposomes, as summarized above, intermingled with fibers throughout the thickness of at least a portion of the paper product. The paper products can be, e.g., units of cardboard or paper. The cardboard or paper can be configured, for example, as a box, an envelope, a mailing tube, a label, a mailbox liner, a mail bag, or a stamp.

In another embodiment, the composite mixture of fibers and bioweapon-sensing agent are applied to an existing woven fabric and allowed to form a mat on the surface of the woven fabric or a mat that is partially or completely intermingled with fibers of the woven fabric.

In yet another embodiment, fibrous threads are spun from a suspension of fibers and bioweapon-sensing agent, yielding threads having the bioweapon-sensing agent interspersed throughout the thickness dimension of the threads. The threads subsequently are formed into a non-woven fabric, a woven fabric, or a composite fabric.

Although fibrous-network products as disclosed herein have especial utility for use in making mail enclosures, it will be understood that the fibrous-network products generally have utility in any of various applications in which detection of bioweapon agents is advantageous.

The foregoing and additional features and advantages of the invention will be more readily apparent from the following detailed description, which proceeds below.

BRIEF DESCRIPTION OF THE FIGURE

FIG. 1 is a schematic diagram of an embodiment of a process for making a paper product in which a bioweapon-sensing agent is dispersed in the thickness dimension of the paper product.

DETAILED DESCRIPTION

I. Abbreviations

UV ultraviolet
XPS x-ray photoelectron spectroscopy
PDA diacetylene monomer
PCA pentacosadiynoic acid monomer
DCDA docosadynoic acid
TRCDA tricosadiynoic acid
SA-PDA sialic acid-derived PDA
OTS octadecyltrichlorosilane
VOC volatile organic chemical
CR colorimetric response
EDC ethylcarboiimide hydrochloride
AFM atomic force microscope
NHS N-hydroxysuccinimide II. General Description of Several Embodiments Disclosed herein are methods for producing fibrous-network products that exhibit a color change in response to contact with one or more specific types of bioweapons (or portions thereof). By way of example, these fibrous-network products are useful for alerting mail-handling personnel and mail recipients after a bioweapon (or portion thereof) has at least contacted the product, and possibly contaminated other items in the postal media or mail-sorting equipment. The color-changed portion of the product can be configured so as to provide mail-handling personnel and mail recipients with an unmistakable indication of the contamination. This, in turn, facilitates the taking of appropriate measures to verify the contamination, contain the contamination, and/or decontaminate the affected item and other possibly affected items and equipment as necessary. Thus, the bioweapon-sensing fibrous-network products disclosed herein facilitate early and reliable detection, containment, and decontamination of bioweapons transmitted through the mail, and can provide reassurance both to postal employees and to mail recipients whenever contamination has not occurred.

The bioweapon-sensitive fibrous-network products disclosed herein have several advantages over the bioweapon-detectors of the prior art. In particular, unlike bioweapon-detectors that are printed on the surface of paper products (e.g., as discussed in U.S. Pat. No. 6,306,598 to Charych et al.), the bioweapon-sensing fibrous-network products disclosed herein contain the bioweapon-sensitive agent dispersed among constituent fibers throughout at least a portion of the thickness of the product. Thus, not only is the bioweapon-sensing agent shielded by fibers from the direct physical insults inherent in the mail-sorting and mail-delivery processes, but also the sensitive agent is available for detecting exposure to a bioweapon (or portion thereof) on both the inside and outside surfaces of the product.

In any of various particularly advantageous embodiments, the bioweapon-sensing fibrous-network product comprises biopolymeric liposomes. The biopolymeric liposomes can be made from a variety of self-assembling monomers such as diacetylene. The liposomes generally are prepared by sonication. (New, *Liposomes: A Practical Approach*, Oxford University Press, Oxford, pp. 33-104 [1990]), although any of various other dispersing techniques or methods can be used. In general, a solution of the self-assembling monomers is prepared. At least most of the solvent is removed. The residual solute is resuspended in an aqueous liquid, and the suspension is sonicated to suspend the monomers in the aqueous liquid. During this suspension, the monomers associate with one another to form liposomes. After liposomes having a desired median size and configuration are formed, sonication is halted, and the monomers are allowed to polymerize to form the biopolymeric liposomes. Biopolymeric liposomes and their production are discussed in greater detail in subsections III and IV, below.

The self-assembling monomers of the biopolymeric liposomes are chemically linked to other molecules (e.g., ligands), that are specific in their ability to interact with one or more types of bioweapon agent contacting the liposomes. Hence, contact of a ligand with a bioweapon agent (or portion thereof) causes the biopolymeric liposome to exhibit a color change. By way of example, a ligand can be used that is sensitive to contact with anthrax organisms or spores, wherein biopolymeric liposomes comprising the ligands exhibit a color change in response to such contact. Further with respect to the example, the "anthrax-sensitive" ligand can be a substrate for a laccase, which is a multi-copper-containing enzyme that catalyzes oxidative conversion of a variety of substrates, including phenols, polyphenols, and aromatic amines. Specific substrates include vanillic acid, syringic acid, and 2-2'-azino-bis(3-ethyl-benzthioazoline-6-sulfonic acid). Incorporating one or more laccase substrates into ligands attached to biopolymeric liposomes yields liposomes that are sensitive to anthrax exposure. In other embodiments, the ligand is an antibody specific for a bioweapon agent or molecule or portion of a bioweapon agent or molecule. Bioweapon-detecting ligands and their attachment to the self-assembling monomers are discussed in greater detail in subsection VI, below.

As an alternative to biopolymeric liposomes, the biopolymeric material can have any of various different forms, wherein particles of biopolymeric material generally are termed "units" of biopolymeric material. The units can be configured as sheets, tubules, or other "regular" shape, or can have any of various "irregular" configurations. For incorporation with fibers from which a fibrous-network product is to be made, the units of biopolymeric material desirably are fragmented or otherwise comminuted to an appropriate mean particulate size. Particular advantages of forming the units of biopolymeric material as liposomes are the very high dimensional uniformity with which liposomes can be formed, and the high strength and robustness of the very small spherical configuration of liposomes.

The biopolymeric materials may further comprise one or more "dopants," which are used to alter and/or to optimize desired properties of the biopolymeric materials. Such properties can include, but are not limited to, colorimetric response, color, sensitivity, durability, amenability to immobilization, temperature sensitivity, and pH sensitivity of the biopolymeric materials. For example, adding sialic acid-derived diacetylene monomers to liposomes comprising ganglioside and PDA causes the liposomes to exhibit increased colorimetric sensitivity to exposure to low levels of particular bioweapons. Dopants, and their inclusion in biopolymeric liposomes, are discussed at greater length in subsection V, below.

Units of the biopolymeric material can be immobilized on or in any of a variety of solid supports, including, but not limited to, polystyrene, polyethylene, Teflon®, silica gel beads, hydrophobized silica, mica, filter paper (e.g., Nylon®, cellulose, and nitrocellulose), glass beads and slides, gold, and various separation media such as silica gel, Sephadex®, and other chromatographic media. Immobilization of the biopolymeric materials can improve, for example, their stability, shelf-life, colorimetric response, color, or other desired properties. In some embodiments, the biopolymeric materials are immobilized in a sol-gel. Immobilization of the biopolymeric liposomes is discussed in greater detail in subsection VII, below.

Manufacture of a bioweapon-sensing fibrous-network product is exemplified by manufacture of a bioweapon-sensing paper product, in which a suspension of units of biopolymeric material is added to a fluid suspension of fibers and mixed to form a composite mixture. The composite mixture is formed into a paper product comprising the units of biopolymeric material and the fibers, wherein the units of biopolymeric material are intermingled with the fibers throughout the thickness dimension of the paper product. In some embodiments, the units of biopolymeric material are intermingled with the fibers throughout a length or a width dimension of the paper product, thereby forming a bioweapon-sensitive stripe or stripes in the paper product. In other embodiments, the units of biopolymeric material are intermingled with the fibers throughout the length and width dimensions of the paper product. The paper product can be, e.g., individual or bound sheets of paper, cardboard or paper configured as a box, an envelope, a tube (e.g., mailing tube), a label, a mailbox liner, a mail bag, or a stamp. Formation of a bioweapon-sensitive paper product is discussed in greater detail below, in subsection VIII.

Whenever the bioweapon-sensitive fibrous-network product contacts a bioweapon agent (or portion thereof), for example during mail-sorting or mail-delivery, the product exhibits a color change in response to the contact. For example, in some embodiments, the color change is from blue to red. In some embodiments, the entire fibrous-network product changes color. In other embodiments, the color change is localized to a particular region of the product, for example, a stripe on an envelope.

The bioweapon-sensitive fibrous-network product can be configured so that the color change is visible to product-handling personnel and/or recipients. Thus, for example, a postal employee or mail recipient can be assured that, for example, if an envelope does not exhibit a changed color, then the envelope has not contacted a detectable dose of the bioweapon to which the envelope is sensitive.

If a bioweapon-sensitive fibrous-network product has contacted a detectable dose of the corresponding bioweapon agent, and the product reveals a characteristic color change, then product-handling personnel or recipients can initiate appropriate steps to verify the contamination, contain the contamination, and/or decontaminate the product and the surrounding environment as necessary. Detection of a bioweapon with the bioweapon-sensitive fibrous-network products disclosed herein is discussed at greater length in subsections IX and X, below.

III. Biopolymeric Materials

Any of various monomers are suitable for forming the biopolymeric material. The monomers can be self-assembling or may require catalysis for assembly. Such monomers include, but are not limited to, acetylenes, carbohydrates, diacetylenes 5,7-docosadiynoic acid, 5,7-pentacosadiynoic acid, and 10,12-pentacosadiynoic acid), alkenes, thiophenes, polythiophenes, imides, acrylamides, methacrylates, vinylether, malic anhydride, urethanes, allylamines, siloxanes, polysilanes, anilines, pyrroles, polyacetylenes, poly-(para-phylenevinylene), poly-(para-phylene), and vinylpyridinium. The monomers as incorporated into lipids can be homopolymers or mixed polymers. Furthermore, the monomers can have any of various head groups including, but not limited to, carboxyl groups, hydroxyl groups, primary amines, amino acid derivatives, and hydrophobic groups. The monomers can be chemically linked to any of various other molecules (e.g., bioweapon-specific ligands).

In some embodiments, lipid monomers comprising diacetylene are used as self-assembling monomers for forming the biopolymeric material. A variety of diacetylene-containing lipid monomers can be used including, but not limited to, 5,7-docosadiynoic acid (5,7-DCDA), 5,7-pentacosadiynoic acid (5,7-PCA), and 10,12-pentacosadiynoic acid (10,12-PCA).

In other embodiments, the biopolymeric material comprises glycopolythiophenes or other polythiophenes that exhibit a color change (e.g., a red-shift) upon binding with one or more specific bioweapon agents. The polythiophenes can be used as such or can include any of various specific receptors, such as polypeptides, lipids, or carbohydrates. An example of such modified polythiophenes is carbohydrate-modified polythiophene (glycopolythiophenes). The glycopolythiophenes, for example, can be further modified for enhanced specificity to a specific bioweapon agent. Modification can include attachment of other carbohydrate lipids, dopants, protein ligands, antibody ligands, and hexokinase ligands.

In order to increase or decrease the sensitivity of the biopolymeric material, the position of a chromophore on the polymer backbone of the biopolymeric material can be varied. For example, bioweapon-sensitivity of a biopolymeric liposome may be increased by moving diacetylene groups of the constituent diacetylene monomers closer to the interfacial region of the liposome. In addition, shorter or longer chain lengths of PDA can affect the sensitivity of the biopolymeric material for detection of a particular bioweapon.

The length of a carbon chain positioning a head group a specific distance from the polymer backbone of the biopolymeric material is dependent on the position of the polymerizable group in the monomer molecules from which the biopolymeric material is formed. In the case of biopolymeric liposomes formed from diacetylene monomers, for example, a diacetylene group positioned from between the 18-20 carbon positions to the 3-5 carbon positions in the monomers, from between the 10-12 carbon positions to the 4-6 carbon positions, or about the 5-7 carbon positions can enhance sensitivity. The production protocol for the monomers determines the final position of the diacetylene group in the monomers used for making the biopolymeric material.

The total carbon-chain length in the monomer also influences the level of sensitivity of biopolymeric material made from the monomer, although generally to a lesser extent than the position of the polymerizable group in the carbon-chain of the monomer. Specifically, a shorter chain length typically confers greater bioweapon-sensitivity. Useful carbon-chain lengths range from between $C_{12}$ to $C_{25}$, although both longer and shorter chain lengths can be used. In some embodiments, the monomer carbon-chain length is $C_{20}$ to $C_{23}$.

IV. Production of Biopolymeric Liposomes as a Representative Biopolymeric Material As noted above, the biopolymeric material used in the present disclosure desirably comprises biopolymeric liposomes. These liposomes desirably are prepared using sonication. (New, *Liposomes: A Practical Approach*, Oxford University Press, Oxford, pp. 33-104 [1990]), although any other method usable for generating liposomes alternatively can be employed. A solution of self-assembling monomers, either alone or in association with a desired ligand, is prepared. At least most of the solvent is removed, and the solute is resuspended in an aqueous liquid. The suspension is sonicated to form the liposomes. The self-assembling monomers in the liposomes are allowed to polymerize.

Liposomes have been described in numerous articles and have been reviewed in texts such as New (supra), and Rosoff, *Vesicles*, Marcel Dekker, New York, [1996]). As noted above, liposomes typically are more stable and robust than films or other structures made of the same biopolymeric material.

In general, liposomes are prepared by dispersing amphiphilic molecules in an aqueous medium. In an aqueous suspension, the constituent amphiphilic molecules of liposomes typically remain in a liquid phase. In an aqueous suspension liposomes can have any of various shapes such as spheres, ellipsoids, squares, rectangles, and tubules (but usually are spherical). In most of these configurations the surface of a liposome is in contact with the aqueous carrier liquid only. If liposomes are "dried" (i.e., if sufficient carrier liquid is removed), they may lose their shape and no longer exist in a liposomal state (i.e., the constituent molecules disassociate and thus no longer are configured as "liposomes").

Hence, the molecules making up the liposomes desirably are polymerized with each other in each liposome, which prevents dissociation and provides substantial liposome stability under various environmental conditions. Polymerization desirably is performed by exposure to ultraviolet (UV) light, which is convenient. Alternatively, polymerization can be performed by application of another suitable source of bonding energy, such as a catalyst or temperature change.

In a biopolymeric liposome, the polymer backbone of the biopolymer will absorb different energies of light, and hence will exhibit a different color, depending upon the degree of polymerization of the biopolymer, the presence of other molecules in the liposomes, and the accessibility of solvent molecules to the biopolymers in the liposome. Such differential absorption of light provides the liposomes with a desired color. The degree of polymerization can be manipulated to provide the liposomes selectively with one or more desired properties. For example, cooling a suspension of liposomes before initiating polymerization can substantially reduce polymerization (cooling to room temperature before initiating polymerization can inhibit UV-initiated polymerization completely). On the other hand, polymerization can be initiated readily in liposomes pre-cooled to 4° C., wherein a subsequent increase in temperature to room temperature has no adverse affect on polymerization. In any event, polymerization usually is evidenced by appearance of, or a change in color of the liposome suspension, e.g., appearance of absorption of light having a wavelength of approximately 630 nm.

As discussed below, binding of a bioweapon molecule or structure situated proximally to the biopolymeric liposome also is detectable through an observable color change of the biopolymeric liposomes (and hence of the fibrous-network product with which the liposomes are incorporated).

V. Dopants

The biopolymeric materials disclosed herein may comprise one or more dopants. Dopants serve to alter and optimize certain properties of the biopolymeric materials. Such properties include, but are not limited to, colorimetric response, color, sensitivity, durability, robustness, amenability to immobilization, temperature sensitivity, and pH sensitivity. For example, the addition of sialic acid-derived diacetylene monomers to liposomes comprising ganglioside and PDA confers to the liposomes a dramatic increase in colorimetric sensitivity of the liposomes with respect to the detection of low levels of certain bioweapons. This improvement in colorimetric response using dopant is extremely beneficial whenever a non-doped biopolymeric material produces a colorimetric response that is too weak to be of practical use.

As noted above, dopants can change the color of the biopolymeric material before and/or after contact with a bioweapon agent to which the biopolymeric material is sensitive. For example, a color change of liposomes is from blue to red (before and after contact, respectively). Other color changes achievable by doping are blue to orange, purple to red, purple to orange, green to red, and green to orange. For example, glutamine-substituted PDA produces very dark blue (i.e., almost black) biopolymeric material. Green biopolymeric material can be produced by application of cycles of annealing (i.e., heating to approximately 80° C.) and cooling (i.e., to room temperature) prior to polymerization. The advantage of altering the color profile (before and after contact) is that fibrous-network products can be made that start at a desired color before contact and exhibit a specific color in response to contact with a specific bioweapon. Multiple dopants can be combined in a single biopolymeric material preparation.

The most appropriate concentration of dopant incorporated with the biopolymeric material depends upon the particular properties desired in the fibrous-network product. For instance, certain applications may require compromised sensitivity in favor of long shelf-life or durability under rigorous field conditions. The acceptable concentration range of dopant is from a concentration having no affect to a concentration that would excessively disrupt the stability of the biopolymeric structures.

By way of example, molar percentages of dopant normally range from 0.01% to 75%. However, certain embodiments may require a percentage of dopant greater than 75% or lower than 0.01%. In some embodiments, a desirable range for dopant is 2%-10%, more desirably about 5%.

In selecting appropriate incorporation methods for the dopant, there are several competing considerations. For example, when producing liposomes by conventional sonication, proper incorporation of large and/or complex dopants typically requires relatively slow and gentle sonication, which may be difficult to accommodate in an industrial process. Also, sonication is most effective whenever only a relatively low concentration of dopant is to be incorporated. Point-probe sonication allows the incorporation of much higher concentrations of dopant over a shorter period of time (typically minutes). However, point-probe sonication typically is limited to incorporation of small to intermediate-sized dopant molecules. The temperature at which dopant incorporation is performed is selected based on the particular liposome parameters desired. A practitioner will be able to select the foregoing and other parameters such as pH, choice of diluents, and other factors based on the particular system and desired characteristics of the biopolymeric material.

VI. Ligands

The biopolymeric materials disclosed herein desirably further comprise one or more types of ligands that act as recognition sites in the biopolymeric materials for specific bioweapon agents. Upon the interaction of a bioweapon molecule or other unit thereof with a ligand or ligands on a molecule of biopolymeric material, a disruption of the polymer backbone of the biopolymeric material occurs, resulting in a detectable chromatic transition (color change) of the biopolymeric material.

A ligand can be linked to a self-assembling monomer or to a biopolymeric material formed from such monomers, by: (1) a linker attached to the self-assembling monomer, (2) a direct linkage to the monomer without using a linker, (3) being incorporated into the biopolymeric material prior to or during polymerization of the monomers, or (4) being attached to the biopolymeric material following polymerization (e.g., by linking ligands to constituents of the biopolymeric material that contain head groups that can be bonded directly to the ligands or via other means).

The ligand can be any of a wide variety of materials. The main criterion is that the ligand have an affinity at least for the bioweapon of choice. Appropriate ligands include, but are not limited to, peptides, carbohydrates, antigens, molecular-recognition complexes, antibodies, or any of various organic molecules that bind to receptors. The biopolymeric material can be formed from combinations of ligand-linked and unlinked monomers, thereby optimizing a desired colorimetric response (e.g., 5% ligand-linked dicosadynoic acid [DCDA] and 95% DCDA having no linked ligands). Additionally or alternatively, multiple ligands can be incorporated into the biopolymeric materials. As is clear from the broad range of ligands that can be used, an extremely diverse group of bioweapons can be detected.

By way of example, the selected ligand is specific for any of various pathogenic organisms and biotoxins, including, but not limited to, anthrax, cryptococcosis, *Escherichia coli*, *Haemophilus influenzae*, brucellosis (undulant fever), coccidioidomycosis (San Joaquin Valley or desert fever), psittacosis (parrot fever), *Yersinia pestis* (the Black Death of the 14th Century), tularemia (rabbit fever), malaria, cholera, typhoid, bubonic plague, cobra venom, shellfish toxin, botulinum toxin, saxitoxin, ricin, smallpox, *Shigella flexneri, S. dysenteriae* (*Shigella bacillus*), *Salmonella, Staphylococcus* enterotoxin B, hemorrhagic fever, Venezuelan equine encephalitis, *Histoplasma capsulatum*, pneumonic plague, Rocky Mountain spotted fever, dengue fever, Rift Valley fever, diphtheria, melioidosis, glanders, tuberculosis, infectious hepatitis, encephalitides, blastomycosis, nocardiosis, yellow fever, typhus, tricothecene mycotoxin, aflatoxin, Q fever, and severe acute respiratory syndrome (SARS).

From the present disclosure, one skilled in the art will be able to select and incorporate an appropriate ligand(s) with biopolymeric materials as disclosed herein. For example, methods for adding any of a diverse range of substituent groups (e.g., carbohydrates, proteins, nucleic acids, and other chemical groups) to lipid molecules are well known in the art. By way of example, the carboxylic acid group on the terminus of a lipid molecule can be easily modified to form an ester, a phosphate ester, an amino group, an ammonium ion, a hydrazine, a polyethylene oxide, an amide, or any of various other compounds. Any of these chemical groups can serve as a site for linking a carbohydrate, a protein, or other chemical group. E.g., a carboxylic acid group on a lipid molecule can be directly linked to a protein by first converting the carboxylic acid group to the corresponding activated ester, followed by reaction of the activated ester with an amine group on a protein molecule to form an amide linkage of the protein to the lipid.

Thus, any of various protein molecules can be attached to biopolymeric liposomes, such as on the surface of the liposomes, thereby providing the liposomes with "protein" ligands. Protein ligands include, but are not limited to, peptides, lipoproteins, glycoproteins, enzymes, receptors, channels, and antibodies. Whenever a molecule or other unit of a corresponding bioweapon binds to the ligand, the polymer backbone of the respective biopolymeric material is subjected to a disruption sufficient to cause the biopolymeric material to exhibit a color change.

For example, *Bacillus anthracis* organisms and spores have laccase activity. The presence of these organisms and spores can be detected by reaction of laccase with a laccase substrate. Laccases are multi-copper-containing enzymes that catalyze oxidation of various substrates, including phenols, poly-phenols, and aromatic amines. Specific laccase substrates include vanillic acid, syringic acid, and 2-2'-azino-bis(3-ethyl-benzthioazoline-6-sulfonic acid). Introducing one or more of these laccase substrates as ligands into the biopolymeric materials of the present disclosure confers a sensitivity of the biopolymeric materials to contact with anthrax organisms and spores.

One of skill in the art will be able to identify other ligands that are useful in detecting other bioweapons, such as antibodies or enzyme substrates specific for the *Variola major* virus that causes smallpox.

VII. Immobilization of Biopolymeric Materials

Units of biopolymeric material can be immobilized on any of variety of solid supports, including, but not limited to, polystyrene, polyethylene, Teflon®, silica gel, hydrophobized silica, mica, filter-paper medium (e.g., Nylon®, cellulose, and nitrocellulose), glass (e.g., glass beads), gold particles, and various separation media such as Sephadex® or other chromatographic or electrophoretic media Immobilization of the biopolymeric material in this manner can improve the stability, shelf-life, colorimetric response, color, and/or other desired properties of the fibrous-network product comprising the biopolymeric material.

In some embodiments, the units of biopolymeric material are immobilized in a sol-gel. For example, biopolymeric liposomes are robust under aqueous conditions and ambient temperatures, but can degrade when exposed to an organic solvent and/or high temperature. Incorporating the biopolymeric liposomes into a sol-gel provides a simple method of immobilizing the liposomes without causing any significant structure modification of the liposomes, thereby creating even more robust structures that can be easily incorporated into a fibrous-network product and/or formed into any desired size or shape.

An exemplary sol-gel can be prepared by sonicating tetramethylorthosilicate, water, and hydrochloric acid until a single-phase solution is obtained. Any of various other metal oxides can be used as an alternative to tetramethylorthosilicate, so long as the selected oxide facilitates the subsequent entrapment of the units of biopolymeric material in the sol-gel and forms sol-gel particles that are sufficiently transparent to allow a color change of entrapped biopolymeric material to be visible or detectable. Such metal oxides include, but are not limited to, silicates, titanates, aluminates, ormosils, and others.

Following sonication, the solution is suitably buffered, and a suspension of units of biopolymeric material, produced as described above, is added to and mixed with the buffered sol-gel suspension. The suspension is poured into a desired molding structure and allowed to congeal. Many types of molding structures can be used to produce gels of any desired size and shape, including, but not limited to, beads, rods, and fibers. Gelation can take place under ambient conditions, or at any other suitable temperature that facilitates the production of the desired sol-gel.

The gelling conditions of the sol-gel preparation can be optimized by varying the gelling temperature, the gel material, and/or the drying conditions to generate a sol-gel having a desired pore size. Control of pore size also can be achieved by suitably varying the degree of cross-linking of the gel. Pore sizes can range from nanometers to hundreds of nanometers or greater. Some gels allow size-selective screening of undesired material while maintaining bioweapon access to the ligand.

After forming the sol-gel, the gel mass is fragmented or comminuted to form particles or fibers suitable for incorporation with other fibers into a fibrous-network product. In an example, DCDA biopolymeric liposomes are incorporated into sol-gel particles, following the sol-gel procedure as described above. Gelation occurs within a few minutes, yielding a sol-gel exhibiting a violet color.

VIII. Incorporation of Units of the Biopolymeric Material into a Fibrous-Network Product Incorporation of units of biopolymeric material (which may or may not be immobilized into a solid support) into a fibrous-network product is exemplified by forming a paper product comprising the biopolymeric material. Formation of the paper product is advantageously performed using a paper-making machine. Alternatively, the paper product can be made by any of various processes by which a fibrous mat is laid down from a fluid suspension (gas or liquid suspension) of fibers and other particles to be incorporated with the fibers into the paper product.

A representative paper-making process is depicted in FIG. 1, in which many of the components will be readily understood by persons of ordinary skill in the relevant art, and hence are not described in detail below. The process begins with a pulper 1. A furnish 2 (fibers to be used to make the paper product) is placed in the pulper 1 along with a suitable carrier liquid 3 (typically water). The carrier liquid 3 can pass through a UV-irradiator 4 to eliminate or reduce bacterial contamination of the carrier liquid before the carrier liquid enters the pulper 1. The carrier liquid 3 desirably has a pH in the range of pH 4-8 as measured by a pH monitor 5. The proper pH can be achieved as a result of the natural pH of the carrier liquid or by appropriate buffering. The suspension of fibers ("slurry") proceeds from the pulper 1 through a slurry tank 6 and machine chest 7. Meanwhile, a suspension of units of the biopolymeric material (e.g., a suspension of biopolymeric liposomes) is stored in a biopolymer-unit tank 13. The slurry dispensed from the machine chest 7 enters the pre mix tank 8 in which the slurry is mixed uniformly with the suspension of units of the biopolymeric material from the biopolymer-unit tank 13 to form a composite mixture. To ensure that the contents of the pre-mix tank 8 are uniformly mixed for use, the pre-mix tank 8 is provided with a nitrogen-sparger 9, an agitator 10, a recirculation loop with inline mixer 11, and an ultrasonic transducer 12. When the composite mixture has a desired concentration of fibers and biopolymeric material, and a desired viscosity, the composite mixture passes from the recirculation loop 11 through a discharge valve 15 to a mix tank 16. The temperature of the mix-tank 16 is controlled by a temperature controller 17 to minimize temperature fluctuations of the composite mixture. From the mix tank 16, the composite mixture is discharged through a screen 18 to a head box 19. From the head box 19, the composite mixture is deposited onto a paper former 20. The paper former 20 is essentially an endlessly moving screen that forms a continuous mat of the fibers and units of biopolymeric material retained on the screen. The carrier liquid passes through the screen, wherein such passage typically is facilitated by application of a vacuum 21. The mat desirably is routed through a dryer 22 comprising multiple rollers 23 in a temperature-controlled housing. As the mat passes through the dryer 22, HEPA-filtered air 24 is directed at the mat to remove residual carrier liquid and thus form the paper product. Desirably, to protect the biopolymeric materials in the paper product, the drying temperature is regulated to less than about 55° C. For example, the drying temperature can be room temperature. To facilitate drying, the dryer 20 can include one or more vacuum-drying pads over which the paper product passes during passage through the dryer. If necessary, the paper product is subjected to ionizers 25 during passage through the dryer to avoid static buildup on the paper product. Following drying, the paper product can be rolled using a winder 26. The recovery system 27 collects and/or recycles from the paper former 20 and/or the screen 18.

The finished paper product produced by the apparatus of FIG. 1 comprises units of biopolymeric material (e.g., biopolymeric liposomes) intermingled with fibers throughout a thickness dimension of the paper product. In some embodiments, the finished paper product comprises the biopolymeric material intermingled with fibers throughout a length or width dimension of the paper product, resulting in a stripe or stripes of bioweapon-sensitive biopolymeric material in the paper product. In other embodiments, the finished paper product comprises units of biopolymeric material intermingled with fibers throughout the length and width dimensions of the paper product, resulting in a uniform distribution of the bioweapon-sensitive biopolymeric material throughout all dimensions of the paper product. In yet other embodiments, the paper product can include any of various other dyes, pigments, and/or additives that can be added to a paper product to achieve desired physical characteristics of the paper product. The paper product can have a thickness and/or weight in the realm of "paper" or a greater thickness and/or weight, such as card stock, cardboard, or the like.

Formation of a fibrous-network product comprising units of the biopolymeric material also is exemplified by forming a woven fabric of threads or yarns made from the fibers. For example, units of biopolymeric material are added to a suspension of suitable fibers from which threads or yarns are spun. As the fibers are spun from the suspension, they incorporate the biopolymeric material through the thickness dimension of the threads or yarns. The threads or yarns are then woven into a fabric containing the units of biopolymeric material. Alternatively, fibrous threads or yarns can be dipped into or sprayed with a suspension of biopolymeric material, and the resulting threads or yarns woven into a fabric. Note that both warp and woof of such fabric need not be of the same threads. Indeed, one thread (e.g., woof) can contain the bioweapon-sensing agent while the other (e.g., warp) does not. Further alternatively, to a woven fabric (which may or may not contain a bioweapon-sensing agent) can be applied a non-woven mat of fibers that contain a bioweapon-sensing agent (or alternatively, a second bioweapon-sensing agent that is different from a first such agent in the woven fabric). Further alternatively, a fabric is formed by felting fibers to which the bioweapon-sensing agent has been added. In all these various embodiments, units of biopolymeric material containing one or more bioweapon-sensing agents are intermingled with fibers of the resulting fibrous-network products through at least a portion of the thickness dimension of the product. A finished fabric created by spinning, weaving, or felting the fibers and particles described herein comprise units of biopolymeric material intermingled with fibers.

In some embodiments, the finished fabric comprises the biopolymeric material intermingled with fibers throughout a length or width dimension of the fabric, resulting in a stripe or stripes of bioweapon-sensitive biopolymeric material in the fabric. In other embodiments, the finished fabric comprises units of biopolymeric material intermingled with fibers throughout the length and width dimensions of the fabric, resulting in a uniform distribution of the bioweapon-sensitive biopolymeric material throughout all dimensions of the fabric. In yet other embodiments, the fabric can include any of various other dyes, pigments, and/or additives that can be added to a fabric to achieve a desired physical characteristic.

After forming the fibrous-network product, it can be subjected to conventional downstream processing to form it into any of various configurations for use, such as office-paper sheets, greeting-card blanks, boxes, envelopes, mailing tubes, labels, mailbox liners, mail bags, or stamps, for example. Woven fabrics and composites comprising the biopolymeric materials described herein are particularly useful for creating durable bioterrorism-detecting fibrous-network products. For example, such a product may be used to form a mailbox liner or mail bag.

IX. Detection of a Bioweapon Agent with Bioweapon-Sensitive Fibrous-Network Products A fibrous-network product as described above exhibits a color change when brought into contact with a specific bioweapon(s) to which the constituent biopolymeric material is sensitive. Such contact causes a corresponding disruption of the polymer backbone of the biopolymeric material. The resulting color change can be detected using any of various methods. For example, a color change is observable simply by visual inspection of the product. Fibrous-network products amenable to visual inspection can be used easily by an untrained person. Alternatively or in addition to visual detectability, a color change in the product can be detected using a colorimetric scanner. The colorimetric scanner can be used for directly detecting a color change or for detecting a specific fluorescence wavelength produced by the product when irradiated with suitable UV light. For example, a barcode reader incorporated into mail-sorting machinery can be configured to detect fluorescence in paper products exposed to a specific bioweapon.

In certain embodiments, a fibrous-network product exposed to a specific bioweapon exhibits a color change from blue (non-exposed) to red (exposed). Other embodiments exhibit other color(s) depending upon various factors discussed above such as type and amount of dopants. The fibrdus-network product can be configured to exhibit the color change locally (e.g., in a stripe) or overall. For example, the paper stock used to form envelopes can be provided with a sensitive stripe or the like that is present in each and every envelope. Contact with a specific bioweapon causes a respective color change in the stripe rather than the entire envelope.

Under most conditions of use, the color change exhibited by the fibrous-network product upon exposure to a respective bioweapon desirably is visible to the user. If the product is used for mail-related purposes, the bioweapon-exposed product would be discernible by mail-handling personnel and/or mail recipients and distinguishable from non-contaminated items. Hence, a postal employee or mail recipient encountering an item of mail not exhibiting a color change is assured that, for example, the item has not been exposed to a detectable dose of anthrax organisms or spores. On the other hand, if a color change has occurred in the mail item, then the person noticing the color change can take prompt action to limit and remove the contamination, such as inspecting other items of mail and limiting contact with suspect mail-sorting and mail-delivery equipment as required.

X. Other Uses

Even though the ligands incorporated into biopolymeric materials used in fibrous-network products as discussed herein desirably are selected based on their respective sensitivity to one or more specific bioweapon agents, it is comprehended that similar ligand-attachment technology can be used to form fibrous-network products that are "sensitive" to contact with any of various other analytes of interest.

The following examples are provided so as to provide further description, and are not intended to be limiting in any way.

EXAMPLES

Example 1

Preparation of Biopolymeric Material

Self-assembling monomers to be incorporated into biopolymeric liposomes are dissolved in respective solvents (e.g., chloroform for diacetylenes and methanol for gangliosides such as $B_{M1}$ used in this example). Any of various other solvents can be used, including, but not limited to, benzene, hexane, and ethylacetate. The solutions are prepared and stored in opaque containers to prevent excessive contact with light. The solutions are combined to yield a lipid mixture of 5% by mole of $G_{M1}$ and 95% by mole of diacetylenes (total lipid content of approximately 2 μmol). After preparing the combined solution, the solvents are evaporated (e.g., by rotary evaporation or using a stream of nitrogen gas).

To the dried solute is added sufficient de-ionized water to produce a 1-15 mM suspension of lipid. The suspension is sonicated to form the lipids into liposomes. The duration of sonication depends upon the type and power output of the sonicator employed (e.g., 15-60 minutes using a Fisher probe sonicator model 300 operated at 50% output, fitted with a microtip). Unless sonication provides sufficient intrinsic heating, the suspension is heated during sonication to heat the suspension to a temperature above the phase-transition temperature of the lipids in the suspension (typically 30-90° C.). The resulting liposome suspension is filtered through a microporous filter and either cooled to 4° C. for storage or immediately subjected to polymerization conditions. Desirably, prior to polymerization, oxygen is removed from the suspension by nitrogen sparging, and nitrogen sparging is continued during polymerization.

Polymerization is performed by exposure to ultraviolet (UV) light (e.g., 254 nm) at a sufficient dose ($J/cm^2$) of light to initiate and propagate the polymerization. Polymerization is continued in this manner for a time sufficient to achieve the desired properties (e.g., color, polymerization degree) of the liposomes.

Example 2

Incorporation, Optimization, and Properties of Dopants

Each bioweapon-sensitive fibrous-network product made as disclosed herein desirably is made with respective concentrations of monomer, dopant, and ligand sufficient to achieve the desired performance. The respective concentrations can encompass wide ranges (e.g., 5-15% ligands, 0-95% PDA, and 0-95% dopant). The percent of each component depends upon the physical characteristics of the fibrous-network product as well as the desired stability and sensitivity of the product to one or more specific bioweapons. Also, as noted above, more than one dopant can be used.

I. Incorporation of Dopant into Biopolymeric Material

A diacetylene dopant (including amino acid substituent groups) and diacetylene monomers are dissolved in chloroform and transferred to a reaction container. The organic solvent is evaporated using $N_2$ gas, and water is added to bring the lipid concentration to approximately 1 mM. The resulting mixture is sonicated to form liposomes. Sonication is performed at approximately 80° C. to facilitate formation of the liposomes and continued for a time sufficient to clarify the mixture. The resulting liposome suspension is immediately filtered (while hot) through a microporous filter to remove particulate impurities. The filtered suspension either can be stored at 4° C. until use or (desirably) used immediately for polymerization.

Polymerization is performed using UV light as noted above, yielding liposomes or other units of biopolymeric material exhibiting a deep-blue color.

II. Properties of Derivatized Diacetylene Dopants

If the amino acid substituent groups in the diacetylene dopant molecules are hydrophobic, then the dopant can be used for reducing the solubility of the biopolymeric material in aqueous media and for reducing the stability of the liposomes. These derivatized PDAs can be useful for fine-tuning the stability and sensitivity of the paper products incorporating the biopolymeric material (stability and sensitivity are directly related to each other). If the units of biopolymeric material contain several types of dopants (e.g., PDAs including hydrophobic amino acid substituent groups and PDAs including hydrophilic amino acid substituent groups), then the stability of the biopolymeric material can be tailored for specific environmental conditions. For example, certain conditions may require high stability with a tolerable reduction in sensitivity. Under most conditions a balance between sensitivity and stability is desired.

Molecules of diacetylene monomers can be linked to acidic and/or basic head groups to increase the solubility of the PDA in a particular liquid(s). Ordinarily, PDA is not water-soluble; a relatively hydrophobic organic solvent is necessary for dissolving PDA. Unfortunately, many hydrophobic organic solvents destroy biological molecules. By linking an acidic or basic head group to a PDA molecule, the solubility of the PDA in a relatively hydrophilic solvent(s) is greatly enhanced. Also, in many instances, biopolymeric materials including these modified PDAs produce brighter colors and hence are more sensitive than liposomes lacking them.

In another example, amine-coupling histidine to PDA creates a dopant that, when incorporated into biopolymeric material, causes the material not only to exhibit a ready color change when exposed to a specific bioweapon but also to be regeneratable. I.e., ordinarily polymerized PDAs exhibit color changes upon exposure, but cannot be reused. The near-neutral $pK_a$ of the head group provided by the linked histidine allows reuse.

In yet another example, amine-coupling fluorescent head groups to PDAs, and incorporating the PDAs in biopolymeric material yields biopolymeric material that exhibits fluorescent properties. Whenever units of such material, incorporated into a fibrous-network product, are brought into contact with a specific bioweapon, the units of biopolymeric material (and thus the fibrous-network product) exhibit a change in fluorescence. This type of product is readily detectable by automated equipment and is suitable for certain covert operations involving mail surveillance, for example.

Example 3

Attachment of Ligands

Ligands desirably are covalently linked (i.e., linked by covalent bonds) to the head groups of self-assembling monomers used for forming the biopolymeric material. Ligands also can be covalently linked to other materials including polymerized materials. For example, proteins and antibodies can be linked with one or more amine and/or thiol linkages to surfaces of liposomes. Ligands also can be non-covalently incorporated into the biopolymeric material (e.g., ganglioside molecules incorporated into liposome membranes).

The synthesis technology for making self-assembling monomers that include any of various head-group functionalities is known in the art. Exemplary head-group functionalities include, but are not limited to, esters, ethers, amino groups, amides, thiols, or combinations thereof. Alternately, ligands can be incorporated by surfactants into self-assembling monomers without covalent linkage (e.g., incorporation of gangliosides and lipoproteins into liposome-membrane regions having multiple hydrophobic moieties).

Specific applications are described below to illustrate the broad range of ligands that can be associated with the biopolymeric material. These examples are intended to be exemplary only, and not limiting in any way.

I. Sialic Acid

In this example, sialic acid is attached as a ligand to diacetylene monomers. Any of several synthesis methods can be used to form the linkage, especially synthesis methods generally useful for attaching carbohydrates to the biopolymeric materials. In a first example, 2.7 mmol PDA in chloroform is reacted with 3 mmol N-hydroxysuccinimide and 3 mmol 1-(3-dimethylaminopropyl)-3-ethylcarbodiimide hydrochloride (EDC). The reaction is allowed to proceed with stirring for 2 hours followed by evaporation of the chloroform. The residue is extracted with diethyl ether and water. The organic layer is dried with magnesium sulfate ($MgSO_4$) and filtered. Residual diethyl ether is evaporated, yielding N-succinimidyl-PDA (NHS-PDA). To a solution of NHS-PDA in chloroform is added ethanolamine (3 mmol), followed by triethylamine (2.5 mmol). The mixture is stirred for two hours at room temperature. The chloroform is evaporated, and the residue is purified by chromatography in silica gel (2:1 EtOAc:hexane, $R_f$=0.15), yielding purified N-(2-hydroxyethyl)-PDA.

The purified N-(2-hydroxyethyl)-PDA is dissolved in chloroform (1.3 mmol), and tetraethylene glycol diamine (6.60 mmol) in chloroform is added dropwise, with stirring, over a period of 30 minutes. The solution is stirred for an additional 30 minutes, and the solvent is evaporated. The residue is dissolved in EtOAc and extracted twice with water. The organic layer is dried with $MgSO_4$, and the chloroform removed by evaporation. The resulting extract is purified by chromatography in silica gel (20:1 $CHCl_3$:MeOH, $R_f$=0.20), yielding purified N-(11-amino-3,6,9-trioxyundecanyl)-PDA.

Approximately equal volumes of acetic anhydride and a cooled solution of ethyl-5-N-acetyl-2,6-anhydro-3,5-dideoxy-2-C-(2-propenyl)-D-erythro-L-manno-nonoate (1.30 mmol) in 1.7 mL of pyridine are mixed together under nitrogen, with stirring. The reaction is allowed to warm to room temperature, followed by removal of the pyridine by application of reduced pressure at ambient temperature. The resulting viscous oil is solidified by repeated evaporation from toluene and flash chromatographed over silica, with ethylacetate as an eluent, to yield purified ethyl-5-N-acetyl-4,7,8,9-tetra-O-acetyl-3,5-dideoxy-2-C-(2-propenyl)-D-erythro-L-manno-nonoate.

A solution of ethyl-5-N-acetyl-4,7,8,9-tetra-O-acetyl-3,5-dideoxy-2-C-(2-propenyl)-D-erythro-L-manno-nonoate (0.72 mmol in acetone) is cooled to −78° C. in the absence of moisture. Ozone is aspirated into the solution until a persistent blue color is obtained. Excess ozone is purged using $O_2$ gas, and the solution is warmed to 5° C. Excess Jones' reagent is added to obtain a persistent rust-orange color, and the solution is further warmed to room temperature. Ethanol is added slowly to consume excess $O_2$ and ozone. The resulting green precipitate is filtered and washed with acetone. The filtrate is evaporated in vacuo and dissolved in ethyl acetate. The solution is extracted with saturated aqueous $NaHCO_3$, and the aqueous phase is acidified with concentrated HCl and extracted with methylene chloride. The methylene chloride extract(s) are dried, filtered, and evaporated in vacuo to yield ethyl-5-N-acetyl-4,7,8,9-tetra-O-acetyl-3,5-didcoxy-2-C-(acetic acid)-D-erythro-L-manno-nonate.

Ethyl-5-N-acetyl-4,7,8,9-tetra-O-acetyl-3,5-dideoxy-2-C-(acetic acid)-D-erythro-L-manno-nonoate (0.35 mmol) is added, under nitrogen, to a 5° C. solution of NHS (0.50 mmol) and EDC (0.50 mmol) in chloroform. The mixture is warmed to room temperature with stirring, diluted with chloroform, and washed with 1 N HCl (aq.), with saturated (aq.) sodium bicarbonate, and with saturated (aq.) sodium chloride. The organic layer is dried over $MgSO_4$, filtered, and evaporated to yield ethyl-5-N-acetyl-4,7,8,9-tetra-O-acetyl-3,5-dideoxy-2-C—(N-succinimidylacetate)-D-erythro-L-manno-nonoate.

Ethyl-5-N-acetyl-4,7,8,9-tetra-O-acetyl-3,5-dideoxy-2-C—(N-succinimidylacetate)-D-erythro-L-manno-nonoate (0.22 mmol) and N-(11-amino-3,6,9-trioxyundecanyl)-PDA (0.24 mmol) are dissolved in chloroform. The mixture is sealed and stiffed for a time sufficient for reaction to progress to completion. The solution is diluted with chloroform and washed with sodium-chloride-saturated 1N HCl (aq.), with saturated (aq.) sodium bicarbonate, and with saturated (aq.) sodium chloride. The organic layer is dried over $MgSO_4$ and filtered. Residual solvent is evaporated, and the resulting semi-solid is flash chromatographed over silica (20:1 $CHCl_3$:MeOH) to yield purified ethyl-5-N-acetyl-4,5,8,9-tetra-O-acetyl-3,5-dideoxy-2-C—[(N-11'-(PDA)-3',6',9'-trioxyundecanyl)acedamido]-D-erythro-L-manno-nonoate.

PDA with sialic acid substituent groups is formed by dissolving ethyl-5-N-acetyl-4,5,8,9-tetra-O-acetyl-3,5-dideoxy-2-C—[(N-11'-(PDA)-3',6',9'-trioxyundecanyl) acedamido]-D-erythro-L-manno-nonoate (0.19 mmol) in a solution of 8:1 (v/v) water:methanol containing sodium hydroxide sufficient to render the solution basic. The solution is stirred, followed by addition of ion-exchange resin (Biorad AG 50W-X4 $H^+$ form) is added until the solution is acidic. The solution is filtered and the filtrate evaporated in vacuo, producing PDA derivatized with sialic acid.

II. Carbohydrates

Carbohydrates (which can include sialic acid) can be modified by a three-step procedure to produce N-allyl glycosides. The N-allyl glycosides can be linked to other molecules (e.g., PDA) using known chemical-synthesis methods. Thus, a broad range of carbohydrates can be incorporated into biopolymeric material (thereby allowing detection of a broad range of bioweapon-related analytes).

The carbohydrates can be obtained from oligosaccharides, in which instance the oligosaccharides are dissolved in neat allyl amine (water may be added if necessary and does not adversely affect the yield) producing a 0.5-0.1M solution of the oligosaccharides that, in the allyl amine, react to form amino glycosides. Upon completion of the reaction, the solvent is removed by evaporation and the remaining solids are washed several times with toluene and evaporated to dryness. The washed solid is chilled, and a solution of 60% pyridine, 40% acetic anhydride is added to yield a solution containing five hundred mole-percent excess of acetic anhydride. The reaction is protected from moisture, stirred, and allowed to warm to room temperature. The solvents are removed by evaporation, and the residue is dissolved in toluene and dried by evaporation several times. The residue is purified by flash chromatography to yield respective peracetylated NAc-allyl-glycoside forms of the free sugars.

The peracetylated NAc-allyl glycosides are dissolved in anhydrous methanol to yield a 0.1-0.01 M solution. A small amount of 1 N NaOMe in MeOH is added and allowed to react. Sufficient Dowex® 50 resin ($H^+$ form) is added to neutralize the base, and the solution is filtered and evaporated to dryness (purification by recrystallization can be conducted if desired). The products are the N-allyl glycosylamide form of the carbohydrates.

The reaction scheme described in this example can be used to produce the respective N-allyl glycosylamide forms of a variety of carbohydrates, including, but not limited to, glucose, NAc-glucosamine, fucose, lactose, tri-NAc-chitotriose, sulfo Lewis analog, and sialyl Lewis analog. Skilled artisans will appreciate the general applicability of this method to the attachment of a broad range of carbohydrates to diacetylene lipids.

III. Ganglioside $G_{M1}$

Ganglioside $G_{M1}$ is exemplary of incorporation of a ligand with self-assembling monomers without covalent attachment of the ligands to the monomers. Ganglioside $G_{M1}$ is introduced by combining a solution of methanol-dissolved ganglioside $G_{M1}$ with chloroform-dissolved PDA. The subsequently dried solution includes a ganglioside that contains a hydrophobic region facilitating its incorporation into self-assembling surfactant structures. Thus, when the dried solution is resuspended in water, structures are formed that contain a mixture of ganglioside and PDA. Liposomes and other structures are produced from the resuspended mixture as described in Example 1. Although the ganglioside does not contain a polymerizable group, the ganglioside becomes embedded in the polymerized matrix created by the cross-linking of the diacetylenes. Similar methods can be used for the incorporation of other ligands containing hydrophobic regions (e.g., transmembrane proteins and lipoproteins) into the biopolymeric material.

IV. Proteins

NHS-PDA produced as described above, thiol-linked PDA, and other compounds provide functional groups useful for attaching proteins and antibodies. The NHS or thiol-linked monomers are incorporated into the liposomes and polymerized, thereby providing NHS or thiol functional groups that provide surface-reaction sites on the liposomes useful for covalently linking proteins and antibodies to the liposomes using known chemical-synthesis reactions. In another embodiment, a hydrazide functional group can be attached to PDA, allowing subsequent linkage of the PDA to aldehydes and ketone groups of proteins and antibodies. Thus, a broad array of proteins and antibodies can be attached to the biopolymeric material. Specific examples are provided below. These examples are not intended to be limiting.

A. Hexokinase

NHS-PDA lipid is synthesized as described above. In brief, 10,12-pentacosadiynoic acid is dissolved in $CHCl_3$, to which N-hydroxysuccinimide (NHS) and 1-(3-dimethylaminopropyl)-3-ethylcarbodiimide hydrochloride are added. After stirring at room temperature, $CHCl_3$ is removed by evaporation. The residue is extracted with EtOAC and water. The organic layer is dried with $MgSO_4$ and filtered, followed by solvent removal. The solids are dissolved in and recrystallized from $CHCl_3$.

Yeast hexokinase suspension is spun in a microcentrifuge to remove saturated ammonium sulfate. The protein is resolubilized in 0.1 M phosphate buffer (pH 8.0) to approximately 1 mg/mL, and dialyzed against the same buffer. PDA-containing liposomes are incubated in the hexokinase solution at 4° C. Prolonged incubation results in decreased color intensity. The liposomes are rinsed with water and immersed into 0.1 M ethanolamine to terminate the linking reaction. The liposomes are rinsed again with water and dried. Polymerization is conducted by irradiation with UV light.

B. Antibodies

Diacetylene is filtered to remove insoluble impurities (e.g., polymerized forms) and converted chemically to NHS-PDA as described above. Appropriate amounts of NHS-PDA and other forms of PDA derivatives (e.g., dopants or ligands) are mixed together at the desired molar ratio. The suspension is dried, and water is added to bring the total concentration of lipid to approximately 1 mM. The solution is sonicated until the liquid is clarified and filtered hot through a microporous filter. The filtrate can be stored at 4° C. until time of use.

Prior to cross-linking, 0.1 M phosphate buffer (pH 8.5) is added to the liposome suspension. A solution of antibody molecules in a similar buffer is then added and allowed to react at 4° C. Excess antibody is removed by either centrifugation or dialysis. If centrifugation is used, the pellet is resonicated gently under ice-bath-temperature conditions. After linking of the antibody molecules to the sonicated material, polymerization is conducted as described for liposomes in Example 1.

Antibodies also can be attached to biopolymeric material by hydrazides. In some embodiments, this manner of antibody attachment may be preferred to NHS-coupling because NHS may react at the Fab' region of the antibody, blocking the ability of the antibody to bind to analytes. The hydrazide method results in attachment of the Fc region of the antibodies to the biopolymeric material, leaving the analyte-binding region of the antibody available for binding to analytes. In the hydrazide method, however, hydrazide-PDA-lipids are produced, along with unpolymerized material.

A stock antibody solution is washed, using Centricon® 50 filters, by adding an equal volume of 123 mM sodium citrate (pH 5.5). The solution is centrifuged, and filtration-washing is repeated. A volume of the antibodies in citrate buffer are oxidized by incubating with sodium periodate at room temperature. The reaction is quenched by addition of N-acetyl-methionine. Next, a mixture of liposomes, citrate buffer, water, and oxidized antibodies is incubated at room temperature to link the antibodies to the liposomes. Unlinked antibodies are removed from the liposomes by filtration-washing with Tris buffer (pH 9.0) and centrifugation. After washing the sample is diluted as required with Tris buffer to make a 0.2 mM (or less) liposome solution.

Any of various other techniques can be used for linking or otherwise associating various molecules to the biopolymeric material. Self-assembling monomers associated with ligands can have modified chain lengths or may consist of double or multiple chains. These various combinations of ligands and monomers provide a broad array of biopolymeric materials appropriate for the interaction with a broad range of analytes, with the desired colorimetric response, selectivity, and sensitivity.

Example 4

Sol-Gel Immobilization of Biopolymeric Material

In this example a silica sol is prepared by sonicating tetramethylorthosilicate (TMOS), water, and 0.04 N aqueous hydrochloric acid under ice-bath-temperature conditions until the solution is one phase. This solution is termed a "sol."

Chilled MOPS buffer solution (50% v/v) is added to the acidic sol under ice-bath-temperature conditions to retard gelation.

Various materials are appropriate for producing silica sols, including, but not limited to, any tetraalkoxysilane or organically modified silane (e.g., ormosil). Additionally, tetraethylorthosilicate (TEOS), methyltriethoxysilane (MeTEOS), aryl silsesquioxanes, and other metal oxides are useful for producing silica sols.

For producing the liposomes, a polymerized liposome solution (produced as described in Example 1) is added to the buffered sol. The mixture can be poured into molds, formed into films, or otherwise allowed to gel at room temperature under sealed conditions. Gelation occurs within a few minutes, resulting in transparent, monolithic units of gel. If the gel contains p-PDA liposomes, then coloration is evident.

Example 6

Colorimetric Analysis

Colorimetric changes of the biopolymeric materials made as described above can be detected by simple visual observation, including by an untrained observer such as an at-home user. Other techniques useful for detecting a color change of the fibrous-network product are set forth below.

I. Visible Absorption Spectroscopy

In some embodiments, it may be preferred to obtain quantitative data pertaining to color changes of the fibrous-network product, or to record subtle changes or faint responses of the product that are undetectable by the human eye.

One manner of performing detections at increased accuracy is by spectroscopy. For example, spectroscopy can be performed of absorption of visible light by the product. For PDA-containing liposomes, a colorimetric response (CR) can be quantified by measuring a percent change in absorption at 626 nm (imparting blue color to the material) relative to an absorption maximum.

The visible-light absorption $B_o$ of a biopolymeric material that has not yet been exposed to an analyte can be expressed as:

$$B_0 = I_{626}/(I_{536} + I_{626})$$

wherein the various "I" variables denote absorption intensity at the respective subscripted wavelengths. The absorption $B_a$ of the biopolymeric material after exposure to the analyte is expressed as:

$$B_a = I_{626}/(I_{536} + I_{626})$$

The colorimetric response (CR) of a liposome solution is defined as the percentage change in the absorption spectrum (B) upon exposure to analyte:

$$CR = [(B_0 - B_a)/B_0](100\%)$$

TERMS

To facilitate an understanding of the present disclosure, a number of terms and phrases are defined below:

"Amino acid" refers to an organic compound having both an amino group ($NH_3$) and a carboxylic acid group (COON) appropriately ionized depending upon the pH of the environment of the amino acid. Amino acids are the essential components of protein molecules.

"Amphiphilic" refers to a molecule having a polar, water-soluble group attached to a non-polar, water-insoluble hydrocarbon chain.

"Analyte" refers to any material that is to be analyzed. Analytes include, but are not limited to, ions, molecules, antigens, bacteria, compounds, viruses, cells, antibodies, and cell parts.

"Antibody" refers to a glycoprotein evoked in an animal by exposure to a complementary immunogen (antigen). An antibody demonstrates specific binding to the respective immunogen, or, more specifically, to one or more epitopes contained in the immunogen.

"Antigen" refers to any molecule, molecular group, or structure that is recognized by at least one antibody. An antigen must contain at least one "epitope" (i.e., the specific biochemical unit capable of being "recognized" by the antibody in a manner resulting in binding of the antibody to the unit).

"Aqueous" refers to a liquid solution or mixture containing water as a solvent or carrier, respectively.

"Bacteria" and "bacterium" refer to any of various prokaryotic organisms, including organisms within various phyla in the Kingdom Procaryotae. The terms encompass all microorganisms commonly regarded as bacteria, including *Mycoplasma, Chlamydia, Actinomyces, Streptomyces*, and *Rickettsia*. The terms also include cocci, bacilli, spirochetes, spheroplasts, protoplasts, etc.

"Biological weapon" or "bioweapon" refers to any of various bacteria, viruses, and toxins that is or can be dispersed deliberately to cause disease or death to humans, animals, or plants, or other biological organisms. Examples of biological weapons include *Bacillus anthracis* that causes anthrax, *Yersinia pestis* that causes plague, and *Variola major* that causes smallpox. Biological weapons also include biotoxins, which any of various poisons produced by certain biological organisms, such as botulinum toxin, produced by the bacterium *Clostridium botulinum*, and ricin, isolated from castor oil seeds.

"Biopolymeric material" refers to a material composed of one or more types of polymerized biological molecules (e.g., lipids, proteins, carbohydrates, and combinations thereof). Biopolymeric materials include, but are not limited to, films, vesicles, liposomes, multilayers, aggregates, membranes, and solvated polymers (e.g., polythiophene aggregates such as rods and coils in solvent). Biopolymeric materials can also comprise unpolymerized molecules.

"Calorimetric" refers to the measurement of heat.

"Carbohydrate" refers to a class of molecules including, but not limited to, sugars, starches, cellulose, chitin, glycogen, and similar structures. Carbohydrates can exist as components of glycolipids and glycoproteins.

"Channel" refers to an integral membrane protein that provides for the regulated transport of a specific ion, or ions, across a membrane.

"Chromatic transition" refers to a change of a molecule or material that results in an alteration of visible-light absorption by the molecule or material. Chromatic transition can refer to a change in light absorption of a sample, whereby a detectable color change of the sample is associated with the transition. Detection of a chromatic transition can be accomplished through various means including, but not limited to, visual observation and spectrophotometry.

"Chromophoric" refers to the property of a chemical group that permits selective light absorption and results in a characteristic coloration.

"Composite product" refers generally to a class of fibrous-network products that include or are made from multiple non-woven fabrics, multiple woven fabrics, or woven and non-woven fabrics integrated together.

"Covalent bond" refers to the linkage of two atoms by the sharing of one or more pairs of electrons by the atoms.

"Derivatize" refers to producing or obtaining a chemical from another substance by chemical reaction.

"Diacetylene monomer" refers to a hydrocarbon molecule containing two alkyne linkages (i.e., carbon/carbon triple bonds).

"Direct colorimetric detection" refers to a detection of a color change without the aid of an intervening processing step (such as conversion of a color change into an electronic signal that is processed by an interpreting device). This term encompasses visual observation (e.g., observation performed directly with the human eye) as well as detection by simple spectrophotometry.

"Dopant" refers to a molecule that, when added to a biopolymeric material, changes a property of the material. Candidate properties include, but are not limited to, calorimetric response, color, sensitivity, durability, amenability to immobilization, temperature sensitivity, and pH sensitivity of the material. Dopant materials include, but are not limited to, lipids, cholesterols, steroids, ergosterols, polyethylene glycols, proteins, peptides, or any other molecule (e.g., surfactants, polysorbate, octoxynol, sodium dodecyl sulfate, zwitterionic detergents, decylglucoside, deoxycholate, diacetylene derivatives, phosphatidylserine, phosphatidylinositol, phosphatidylethanolamine, phosphatidylcholine, phosphatidylglycerol, phosphatidic acid, phosphatidylmethanol, cardiolipin, ceramide, cerebroside, lysophosphatidylcholine, D-erythroshingosine, sphingomyelin, dodecyl phosphocholine, N-biotinyl phosphatidylethanolamine, polyethylene glycol, peptide detergents, 3-[-(cholamidopropyl)dimethylammonio]-1-propanesulfonate, and other synthetic or natural components of cell membranes) that can be associated with a membrane (e.g., liposomes).

"Encapsulate" refers to encompassing, encasing, or otherwise associating two or more materials with each other in a manner such that an encapsulated material is immobilized within or onto a respective encapsulating material.

"Enzyme" refers to a biological molecule or molecular aggregate that catalyzes a chemical or biological reaction. Enzymes are typically proteins, but "enzyme" can also comprise any of various short peptides, RNAs, ribozymes, antibodies, and other molecules.

"Furnish process" refers generally to a paper-making process.

"Glycolipid" refers to a lipid containing a carbohydrate group.

"Glycoprotein" refers to a protein containing a carbohydrate group.

"Head group" refers to a molecular groups situated at an end of a molecule (e.g., a carboxylic acid group at the end of a fatty acid).

"Homopolymer" refers to a polymer formed by the bonding together of multiple units of a single type of molecular species (i.e., a single "monomer").

"Hydroxyl group" refers to the univalent radical or group, OH, which is a characteristic component of bases, certain acids, phenols, alcohols, carboxylic and sulfonic acids, and amphoteric compounds.

"Immunogen" refers to any molecule, compound, or structure that induces the production of antibodies by an antibody-producing organism. By definition, an immunogen must contain at least one epitope.

"Interfacial region" refers to the region between two plane surfaces or faces, particularly two membrane faces.

"Ligand" refers to any ion, molecule, molecular group, or other substance that binds to another molecule or molecular structure, usually in a specific manner. Examples of ligands include, but are not limited to, ions, charged molecules, peptides, carbohydrates, nucleic acids (e.g., DNA and RNA), antibodies, or any of various molecules that bind to receptors.

"Lipid" refers to any of various compounds that are soluble in a hydrophobic organic solvent. Lipids include, but are not limited to, fats, waxes, steroids, sterols, glycolipids, glycosphingolipids (including gangliosides), phospholipids, terpenes, fat-soluble vitamins, prostaglandins, carotenes, and chlorophylls.

"Lipoprotein" refers to any of various conjugated proteins in which at least one of the components is a lipid.

"Liposome" refers to a spherical lipid complex that can be induced to segregate out of aqueous media.

"Mixed polymer" refers to a material comprised of two or more types of polymers.

"Molecular-recognition complex" refers to any molecule, molecular group, or molecular complex that is capable of recognizing (i.e., specifically interacting with) a particular molecule. For example, the ligand-binding site of a receptor is a molecular-recognition complex.

"Paper product" refers generally to a class of fibrous-network products that are non-woven, typically made from cellulosic and/or non-cellulosic fibers laid down from a fluid suspension of the fibers. The fibers can be obtained from pulp containing wood fibers, cotton fibers, grass fibers, and/or other natural fibers. Alternatively or in addition, the fibers can be non-cellulose polymeric, mineral, glass, or other fibers. Paper products generally are processed into leaves, sheets, rolls, or other units by deposit of the fibers from a fluid suspension of the fibers with binders and other additives as required. Paper products can include, but are not limited to, paper leaves (sheets), cards, envelopes, boxes, tubes, labels, mailbox liners, mail bags, and stamps.

"Paper pulp" refers to a suspension of cellulose pulp used for making a paper product.

"Peptide" refers to two or more amino acids covalently joined by peptide bonds.

"Polymer" refers to any of numerous natural and synthetic compounds composed of repeated linked units, each a relatively light and simple molecule.

"Polymerizable group" refers to a chemical group that is capable of undergoing polymerization.

"Polymerization" refers to the uniting of two or more monomers to form a polymer.

"Postal media" refers to any of various media used in the delivery of mail and parcels. Postal media can include, but are not limited to, paper, cardboard, envelopes, boxes, mailing tubes, labels, mailbox liners, mail bags, and stamps.

"Primary amine" refers to derivatives of ammonia in which one hydrogen has been replaced by a hydrocarbon unit. Some common primary amines are aniline, methylamine, and 1-propylamine.

"Protein" refers broadly to any of various molecules or molecular assemblies containing two or more amino acids linked together by a peptide bond. Proteins include, but are not limited to, peptides, enzymes, antibodies, receptors, lipoproteins, and glycoproteins.

"Pulper" refers to a step in a paper-manufacturing process in which paper pulp is suspended in water to form a slurry.

"Receptor" refers to a grouping on a macromolecule or a cell which can combine selectively with other complementary molecules or cells (e.g., enzyme receptors or cell surface receptors for hormones or growth factors).

"Room temperature" refers to a temperature approximately between 20 and 25 degrees centigrade.

"Self-assembling monomer" refers to molecules that spontaneously associate to form molecular assemblies, such as surfactant molecules that associate to form surfactant molecular assemblies. Self-assembling monomers include single molecules (e.g., molecules of a single type of lipid) and small molecular assemblies (e.g., molecules of polymerized lipids), that can be further aggregated (e.g., assembled and polymerized) into larger molecular assemblies.

"Slurry" refers to a suspension of any of various particulate substances, such as cement, plaster of Paris, clay, or cellulose fibers, in a carrier liquid.

"Sol-gel" refers to a colloidal suspension of silica particles that is gelled to form a solid. The resulting gel is porous, and can have biological or other material entrapped within the porous structures.

"Sol-gel material" refers to any material prepared by a sol-gel process, including the sol-gel itself and any material entrapped within the sol-gel.

"Sol-gel process" refers to any method that results in the production of a sol-gel. The materials used to produce the sol-gel can include, but are not limited to, aluminates, aluminosilicates, titanates, ormosils (organically modified silanes), metal oxide glasses, and other metal oxides.

"Solid support" refers to a solid object or surface upon which a sample is layered, attached or. Solid supports include, but are not limited to, glass, metals, gels, and filter paper, among others.

"Substrate," in one sense, refers to a material or substance on which an enzyme or other reaction means acts. In another sense, it refers to a surface on which a sample grows or is attached.

"Ultraviolet irradiation" (UV radiation) refers to exposure to radiation with wavelengths less than that of visible light (i.e., less than approximately 360 nM) but greater than that of X-rays (i.e., greater than approximately 0.1 nM). Ultraviolet radiation possesses greater energy than visible light and is therefore, more effective at inducing photochemical reactions.

"Woven product" refers generally to a class of fibrous-network products that are made by weaving (e.g., by weaving warp and woof or by knitting) threads or yarns to form a fabric. The threads or yarns are formed of or comprise any of the various types of fibers listed in the definition of "paper product," above.

Whereas the invention has been described above in connection with multiple representative embodiments, it will be understood that the invention is not limited to those embodiments. On the contrary, the invention is intended to encompass all modifications, alternatives, and equivalents as may be included within the spirit and scope of the invention, as defined by the appended claims.

What is claimed is:

1. A method for producing a biological-weapon-sensing fibrous-network product, comprising-the steps:
    adding units of a biological-weapon-sensing agent to a suspension of fibers suitable for making a fibrous-network product;
    mixing the units of the biological-weapon-sensing agent with the fiber suspension to form a mixture; and
    forming the mixture into a fibrous-network product comprising the fibers and the units of biological-weapon-sensing agent intermingled with the fibers through at least a part of a thickness dimension of the fibrous-network product, thereby producing the biological-weapon-sensing fibrous-network product,
    wherein the units of biological-weapon-sensing agent comprise units of biopolymeric material;
    wherein the units of biopolymeric material comprise biopolymeric liposomes; and
    wherein the biological-weapon-sensing agent comprises biopolymeric liposomes encapsulated in a transparent sol-gel.

2. The method of claim 1, wherein the fibers in the suspension include cellulosic fibers.

3. The method of claim 1, wherein the fibrous-network product is a paper product.

4. The method of claim 3, wherein the paper product is formed using a paper-making machine.

5. The method of claim 1, wherein the units of biological-weapon-sensing agent are sensitive to contact with more than one type of biological weapon.

6. The method of claim 5, wherein the units of biological-weapon-sensing agent exhibit respective color changes upon contact with a first type of biological weapon and upon contact with a second type of biological weapon.

7. The method of claim 1, wherein the units of biological-weapon-sensing agent exhibit a color change upon contact with a biological weapon to which the units are sensitive.

8. The method of claim 1, wherein the fibers in the suspension include at least one of cellulosic fibers and noncellulosic fibers.

9. The method of claim 8, wherein the fibrous-network product is a paper product.

10. The method of claim 9, wherein the paper product is formed using a paper-making machine.

11. A method for producing a biological-weapon-sensing paper product, comprising-the steps:
    creating a suspension of fibers as a portion of a paper-fiber slurry, wherein the fibers in the suspension include at least one of cellulosic fibers and noncellulosic fibers
    adding a suspension of biological-weapon-sensing biopolymeric liposomes to the paper-fiber slurry;
    mixing the biopolymeric liposome suspension with the paper-fiber slurry to form a composite mixture;
    forming the composite mixture into a paper comprising the biopolymeric liposomes and paper fibers, wherein the liposomes are intermingled with the paper fibers through a thickness dimension of the paper, thereby producing a biological weapons-sensing paper product; and
    wherein the biological-weapon-sensing biopolymeric liposomes are encapsulated by a transparent sol-gel.

12. The method of claim 11, wherein the biopolymeric liposomes are distributed throughout a length dimension of the paper product.

13. The method of claim 11, wherein the biopolymeric liposomes are distributed throughout a width dimension of the paper product.

14. The method of claim 11, wherein the biopolymeric liposomes are distributed throughout a length and width dimension of the paper product.

15. The method of claim 11, wherein the biopolymeric liposomes are immobilized on particles of a solid support medium distributed through the thickness dimension of the paper product.

16. The method of claim 1, wherein mixing the units of biopolymeric liposomes with the fiber suspension comprises mixing an aqueous suspension of the fibers with a suspension of the transparent sol-gel encapsulated biopolymeric liposomes.

17. The method of claim 11, wherein mixing the aqueous suspension of the fibers with the suspension of the transparent sol-gel encapsulated biopolymeric liposomes comprises agitating the aqueous suspension of the fibers and the suspension of the transparent sol-gel encapsulated biopolymeric liposomes.

18. The method of claim 17, further comprising drying the fibrous-network product in a dryer, wherein the dryer comprises a first set of rollers spaced apart horizontally from a second set of rollers, and the drying comprises pulling the fibrous-network product vertically upward through the first set of rollers and vertically downward through the second set of rollers.

19. A method for producing a biological-weapon-sensing paper product, comprising-the steps:
  creating a suspension of fibers as a portion of a paper-fiber slurry, wherein the fibers in the suspension include at least one of cellulosic fibers and noncellulosic fibers;
  adding a suspension of biological-weapon-sensing biopolymeric liposomes to the paper-fiber slurry;
  mixing the biopolymeric liposome suspension with the paper-fiber slurry to form a composite mixture;
  forming the composite mixture into a paper comprising the biopolymeric liposomes and paper fibers, wherein the liposomes are intermingled with the paper fibers through a thickness dimension of the paper, thereby producing a biological weapons-sensing paper product; and
  further comprising encapsulating biopolymeric liposomes in a transparent sol-gel.

20. The method of claim 11, wherein adding the suspension of biological-weapon-sensing biopolymeric liposomes to the paper-fiber slurry comprises mixing the paper-fiber slurry with a suspension of the transparent sol-gel encapsulated biopolymeric liposomes.

21. The method of claim 20 wherein mixing the paper-fiber slurry with the suspension of the transparent sol-gel encapsulated biopolymeric liposomes comprises agitating the slurry and the suspension of the transparent sol-gel encapsulated biopolymeric liposomes.

22. The method of claim 21, further comprising drying the paper in a dryer, wherein the dryer comprises a first set of rollers spaced apart horizontally from a second set of rollers, and the drying comprises pulling the paper vertically upward through the first set of rollers and vertically downward through the second set of rollers.

23. The method of claim 11, wherein producing a biological weapons-sensing paper product having liposomes intermingled with the paper fibers through a thickness dimension of the paper creates biopolymeric liposomes within the paper such that following physical insult to biopolymeric liposomes at a surface of the paper, the biopolymeric liposome within the paper are exposable at the surface, thereby imparting biological weapons-sensing endurance to the paper and eliminating the need to preliminarily identify or collect suspicious samples.

24. The method of claim 19, wherein producing a biological weapons-sensing paper product having liposomes intermingled with the paper fibers through a thickness dimension of the paper creates biopolymeric liposomes within the paper such that following physical insult to biopolymeric liposomes at a surface of the paper, the biopolymeric liposome within the paper are exposable at the surface, thereby imparting biological weapons-sensing endurance to the paper and eliminating the need to preliminarily identify or collect suspicious samples.

25. The method of claim 19, wherein adding the suspension of biological-weapon-sensing biopolymeric liposomes to the paper-fiber slurry comprises mixing the paper-fiber slurry with a suspension of the transparent sol-gel encapsulated biopolymeric liposomes.

26. The method of claim 25, wherein mixing the paper-fiber slurry with the suspension of the transparent sol-gel encapsulated biopolymeric liposomes comprises agitating the slurry and the suspension of the transparent sol-gel encapsulated biopolymeric liposomes.

27. The method of claim 26, further comprising drying the paper in a dryer, wherein the dryer comprises a first set of rollers spaced apart horizontally from a second set of rollers, and the drying comprises pulling the paper vertically upward through the first set of rollers and vertically downward through the second set of rollers.

28. The method of claim 19, wherein the biopolymeric liposomes are distributed throughout at least one of a length dimension and a width dimension of the paper product.

29. The method of claim 19, wherein the biopolymeric liposomes are immobilized on particles of a solid support medium distributed through the thickness dimension of the paper product.

* * * * *